US00PP18175P2

(12) United States Plant Patent
Van Spronsen

(10) Patent No.: US PP18,175 P2
(45) Date of Patent: Oct. 30, 2007

(54) ***CHRYSANTHEMUM* PLANT NAMED 'POWER YELLOW'**

(50) Latin Name: *Dendranthemum×grandiflora*
Varietal Denomination: Power Yellow

(75) Inventor: Steven Van Spronsen, Niagara on the Lake (CA)

(73) Assignee: Willy's Greenhouse Ltd., Ontario (CA)

( * ) Notice: Subject to any disclaimer, the term of this patent is extended or adjusted under 35 U.S.C. 154(b) by 4 days.

(21) Appl. No.: 11/442,883

(22) Filed: May 30, 2006

(51) Int. Cl.
*A01H 5/00* (2006.01)

(52) U.S. Cl. ..... Plt./295

(58) Field of Classification Search ..... Plt./295
See application file for complete search history.

*Primary Examiner*—Kent Bell
*Assistant Examiner*—Annette H Para
(74) *Attorney, Agent, or Firm*—Penny J. Aguirre

(57) ABSTRACT

A new cultivar of *Chrysanthemum*, 'Power Yellow', characterized by it's early and free flowering habit, its daisy-type inflorescences with yellow ray florets and bright yellow disk florets, its vigorous freely branched growth habit, its small leaved dark green foliage and its uniform, rounded and outward spreading plant habit.

2 Drawing Sheets

Botanical classification: *Dendranthemum×grandiflora.*
Variety denomination: 'Power Yellow'.

BACKGROUND OF THE INVENTION

The present invention relates to a new and distinct cultivar of *Chrysanthemum* plant, botanically known as *Dendranthemum×grandiflora* 'Power Yellow' (syn. *Chrysanthemum×morifolium*) and hereinafter by its cultivar name, 'Power Yellow'.

The new *Chrysanthemum* 'Power Yellow' was discovered as a naturally occurring whole plant mutation of the *Chrysanthemum* cultivar 'Apricot Cherie' (U.S. Plant Pat. No. 12,961). The new *Chrysanthemum* was selected as unique by the inventor as a single flowering plant within a population of the parent variety in March 2005 in Niagara on the Lake, Ontario, Canada.

In comparison to the parent plant, 'Apricot Cherie', 'Power Yellow' has yellow-colored ray florets whereas 'Apricot Cherie' has tan colored ray florets. 'Power Yellow' has similar characteristics to the parent in growth habit and flowering response, which distinguishes itself from other cultivars of *Chrysanthemum* with yellow colored ray florets. In comparison to the cultivar, 'Yellow Cherie' (U.S. Plant Pat. No. 9,713), 'Power Yellow' differs in having a larger plant size, yellow ray florets that are deeper in color, and a different blooming time. 'Power Yellow' begins to bloom about one week later than 'Yellow Cherie'.

Asexual reproduction of the new cultivar was first accomplished via stem cuttings in March 2005 in Niagara on the Lake, Ontario, Canada. The characteristics of this cultivar have been determined to be stable and are reproduced true to type in successive generations.

SUMMARY OF THE INVENTION

The following traits have been repeatedly observed and are determined to be the characteristics of the new cultivar of *Chrysanthemum.* These attributes in combination distinguish by 'Power Yellow' as unique from all other varieties of *Chrysanthemums* known to the inventor.

1. 'Power Yellow' is early flowering with daisy-type inflorescences about 4.5 cm in diameter.
2. The inflorescences of 'Power Yellow' have yellow ray florets with bright yellow disk florets that open from bronze colored buds.
3. 'Power Yellow' has a freely branched, uniform, rounded and outward plant habit.
4. 'Power Yellow' has a uniform flowering response.
5. 'Power Yellow' has small leaved dark green foliage.
6. 'Power Yellow' is a vigorous grower.

BRIEF DESCRIPTION OF THE DRAWINGS

The accompanying colored photographs illustrate the overall appearance and distinct characteristics of the new *Chrysanthemum*, 'Yellow Power'. The photographs were taken of a plant grown in a 5-inch pan pot planted with 3 rooted cuttings and grown under greenhouse conditions for 10 weeks.

Figure 1:
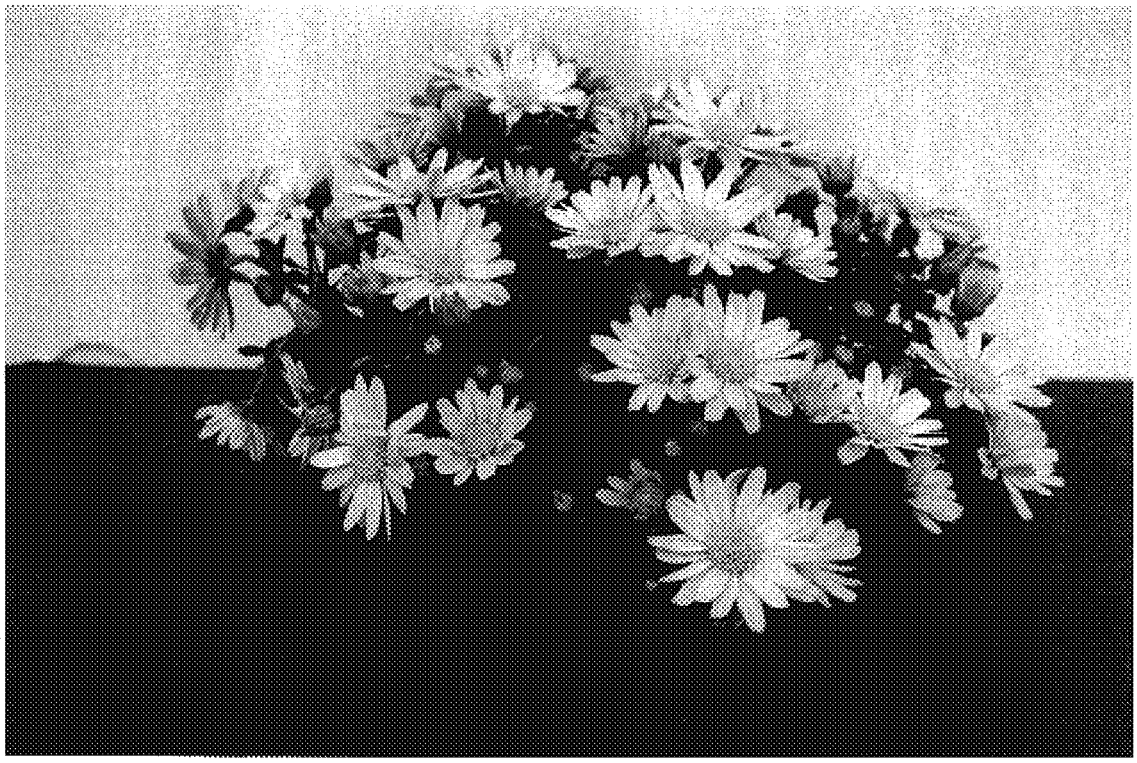
FIG. 1 is a photograph that provides a side perspective view of a typical plant in bloom when grown as a spray-type.
Figure 2:
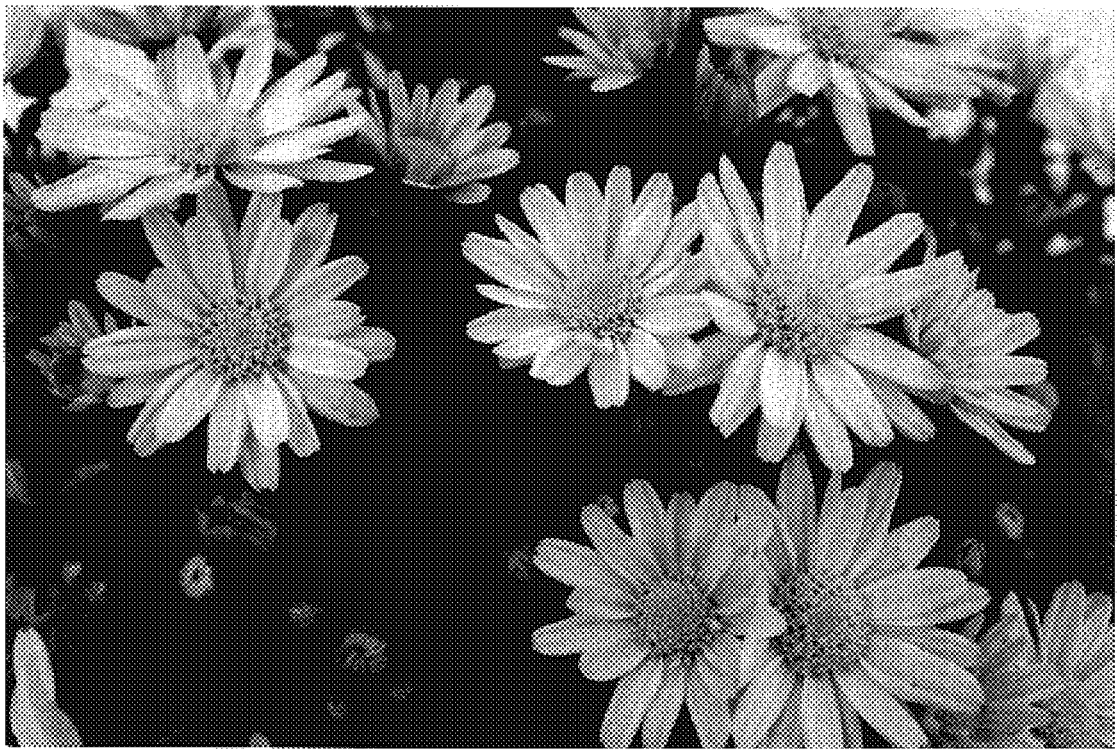

The photograph in FIG. 2 provides a close-up view of the inflorescences of 'Power Yellow'.

The colors in the photographs are as close as possible with the photographic and printing technology utilized. The color values cited in the detailed botanical description accurately describe the colors of the new *Chrysanthemum.*

DETAILED BOTANICAL DESCRIPTION

The following is a detailed description of plants of the new cultivar as grown in a 5-inch pan pot planted with 3 pinched rooted cuttings and grown under greenhouse conditions at an average temperature of 65° F. for 10 weeks. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Botanical classification.*—*Dendranthemum*× *grandiflora* (syn. *Chrysanthemum*×*morifolium*).

*Commercial classification.*—Daisy-type potted *Chrysanthemum.*

*Flowering response.*—Early blooming, flowering occurs after short day treatment in about 52 days in spring, summer and fall and 56 days in winter.

*Plant type.*—Herbaceous, grown as a potted *Chrysanthemum* as a spray-type.

*Plant habit.*—Freely branched, uniform, outward plant habit with rounded crown.

*Height and spread.*—Reaches about 16 cm in height and 30 cm in width when grown under the conditions tested under greenhouse conditions.

*Diseases resistance.*—No susceptibility or resistance to diseases common to *Chrysanthemum* has been observed under commercial greenhouse productions.

*Root description.*—Fibrous.

Growth and propagation:

*Propagation.*—Terminal stem cuttings.

*Time to root.*—About 10 days at 70° F.

*Production.*—Rooted cuttings grown on at 65° F. finish in a 5-inch pan pot in 8 weeks.

*Growth rate.*—Vigorous.

Stem description:

*Stem color.*—144A.

*Stem strength.*—Strong and flexible.

*Stem surface.*—Pubescent.

*Branching habit and quantity.*—Freely branched, about 5 branches per stem after removal of the apical meristem (pinching).

*Lateral branch size.*—About of 12 cm in length and about 3 mm in width.

*Internode length.*—Average of 1 cm.

Foliage description:

*Leaf division.*—Simple.

*Leaf shape.*—Blade is broadly ovate with narrowing towards base.

*Leaf base.*—Cuneate to truncate.

*Leaf apex.*—Rounded and mucronate.

*Leaf margin.*—Palmately incised up to 1 cm deep.

*Leaf texture.*—Upper surface slightly pubescent, lower surface pubescent.

*Leaf venation.*—Upper surface 144B, lower surface 138B.

*Leaf attachment.*—Sessile.

*Leaf arrangement.*—Alternate.

*Leaf number.*—Average of 18 per lateral branch.

*Leaf color.*—Young foliage; upper surface 137A, lower surface 137C, mature foliage; upper surface 137A, lower surface a color between 137B and 191A.

*Leaf size* (*fully expanded*).—Average of 4 cm in length and 3.2 cm in width.

*Fragrance of foliage.*—Fragrant if bruised.

Flower description:

General description:

*Inflorescence type.*—Composite, daisy form with oblong shaped ray florets and disk flowers arranged acropetally on a capitulum, inflorescences typically borne in compound corymbs.

*Postproduction longevity.*—Conditions dependent, Inflorescences maintain good color and substance for about 2 weeks in an interior environment.

*Fragrance.*—None.

*Quantity of inflorescences.*—Average of 16 per lateral stem, about 240 per plant produced from 3 cuttings.

*Inflorescence buds.*—About 1.2 cm in depth and 8 mm in diameter, initially globose becoming ovate before opening, color 19D with blush of 180C and phyllaries 138A.

*Inflorescence size.*—About 1.2 cm in depth and 4.5 cm in diameter, diameter of disk about 1.1 cm.

*Peduncle.*—Strong, flexible, held at an angle of 45° to 55° to vertical, texture is pubescent, first peduncle is an average of 3 cm in length and fourth peduncle is an average of about 4.5 cm in length, color is 138B.

*Involucral bracts* (*phyllaries*).—Arranged in two layers, 137A in color with translucent margins, about 4 mm in length, about 1 to 1.2 mm in width, slightly pubescent in texture.

*Receptacle.*—About 4 mm in diameter, 144D in color.

Ray florets (capitulate):

*Number.*—Average of 20.

*Arrangedment.*—In 2 rows.

*Shape.*—Elongated oblong.

*Aspect.*—Held at about 80° C. from vertical when fully open.

*Size.*—Average of 2 cm in length and 5 mm in width.

*Petal apex.*—Rounded with top mucronulate or notched.

*Petal base.*—Cuneate.

*Petal margins.*—Entire.

*Petal texture.*—Glabrous on upper and lower surface.

*Petal color.*—Opening; Upper surface 7C, lower surface 7D with center blushed with 180D, fully open; upper and lower surface 7D with center blushed with 180D, Fading; upper and lower surface 8B.

Disk florets (perfect):

*Arrangement.*—Massed in center of receptacle.

*Quantity.*—Average of 93.

*Shape.*—Tubular.

*Size.*—About 5 mm in length and about 1 mm in width at base and 3 mm at apex.

*Color.*—Immature 1B, mature 7A.

Reproductive organs:

*Presence.*—Disk flowers are perfect, ray flowers are carpellate.

*Gynoecium.*—1 Pistil per disk and ray floret, 5 mm in length, style color 144D, stigma 7C.

*Androcoecium.*—1 stamen per disk floret, fused into tube surrounding style, anther color 12A, pollen is scarce and 13A in color.

*Seed.*—Seed production has not been observed under conditions tested.

I claim:

1. A new and distinct cultivar of *Chrysanthemum* plant named 'Power Yellow' as herein illustrated and described.

* * * * *